United States Patent [19]
Jones et al.

[11] Patent Number: 5,510,006
[45] Date of Patent: Apr. 23, 1996

[54] PROCESS FOR SEPARATION OF VANILLIN BY MEANS OF AZEOTROPIC DISTILLATION WITH DIBENZYL ETHER

[75] Inventors: Thomas Jones, Rahway; Jeffrey L. Finnan, Maplewood; Joseph Arvizzigno, Scotch Plains, all of N.J.

[73] Assignee: International Flavors & Fragrances Inc., New York, N.Y.

[21] Appl. No.: 450,303

[22] Filed: May 25, 1995

[51] Int. Cl.$^6$ .................................................. B01D 3/36
[52] U.S. Cl. ........................ 203/48; 203/63; 568/438
[58] Field of Search ........................ 203/48, 63, 57, 203/91; 252/DIG. 9; 23/300; 568/438; 426/650

[56] References Cited

U.S. PATENT DOCUMENTS

| | | | |
|---|---|---|---|
| 3,049,566 | 8/1962 | Schoeffel et al. | 568/438 |
| 3,686,322 | 8/1972 | Diddams et al. | 568/438 |
| 4,090,922 | 5/1978 | Bauer et al. | 203/48 |
| 4,351,962 | 9/1982 | Gradeff et al. | 568/438 |
| 4,474,994 | 10/1984 | Makin | 203/39 |
| 5,382,329 | 1/1995 | Berg | 203/60 |
| 5,382,330 | 1/1995 | Berg | 203/60 |
| 5,401,366 | 3/1995 | Berg | 203/57 |

OTHER PUBLICATIONS

Arnaud, et al., entitled "étude des gousses des vanille Madagascar/critéres analytiques de la récolte 1981", published by parfums, cosmétiques, arômes, No. 53, Oct.–Nov. 1983, pp. 99–101. Trnaslation into the English Language.

Derbesy, et al., entitled "contribution " létude des gousses de vanille/Critéres analytiques de différents lots de gousses Madagascar, Récolte 1980", published by parfums, cosmétiques, arômes, No. 43, Feb.–Mar. 1983, pp. 73–77. Translation into the English language.

Cela, et al., *Chemical Abstracts*, vol. 107:108522p, published 1986.

Arnaud, et al, *Chemical Abstracts*, vol. 100:101716b, published 1983.

Buil, et al, parfums, cosmétiques, arômes, No. 52, Aug.–Sep. 1983, pp. 45–49, entitled: "Newly Identified Constituents in Concrete from Carnation Flowers".

Horsley, et al, entitled "Azeotropic Data", No. six of the "Advances in Chemistry Series"/American Chemical Society, published Jun. 1952, front cover page, pp. 1, 2, 218, 219 and 249 of interest.

*Primary Examiner*—Virginia Manoharan
*Attorney, Agent, or Firm*—Arthur L. Liberman

[57] ABSTRACT

Vanillin is difficult to separate from second organic chemicals produced therewith such as parahydroxybenzaldehyde by conventional distillation or rectification because of the proximity of their boiling points. Vanillin can now be readily separated from such second organic chemicals by azeotropic distillation using as an effective azeotropic distillation agent, dibenzyl ether.

4 Claims, 14 Drawing Sheets

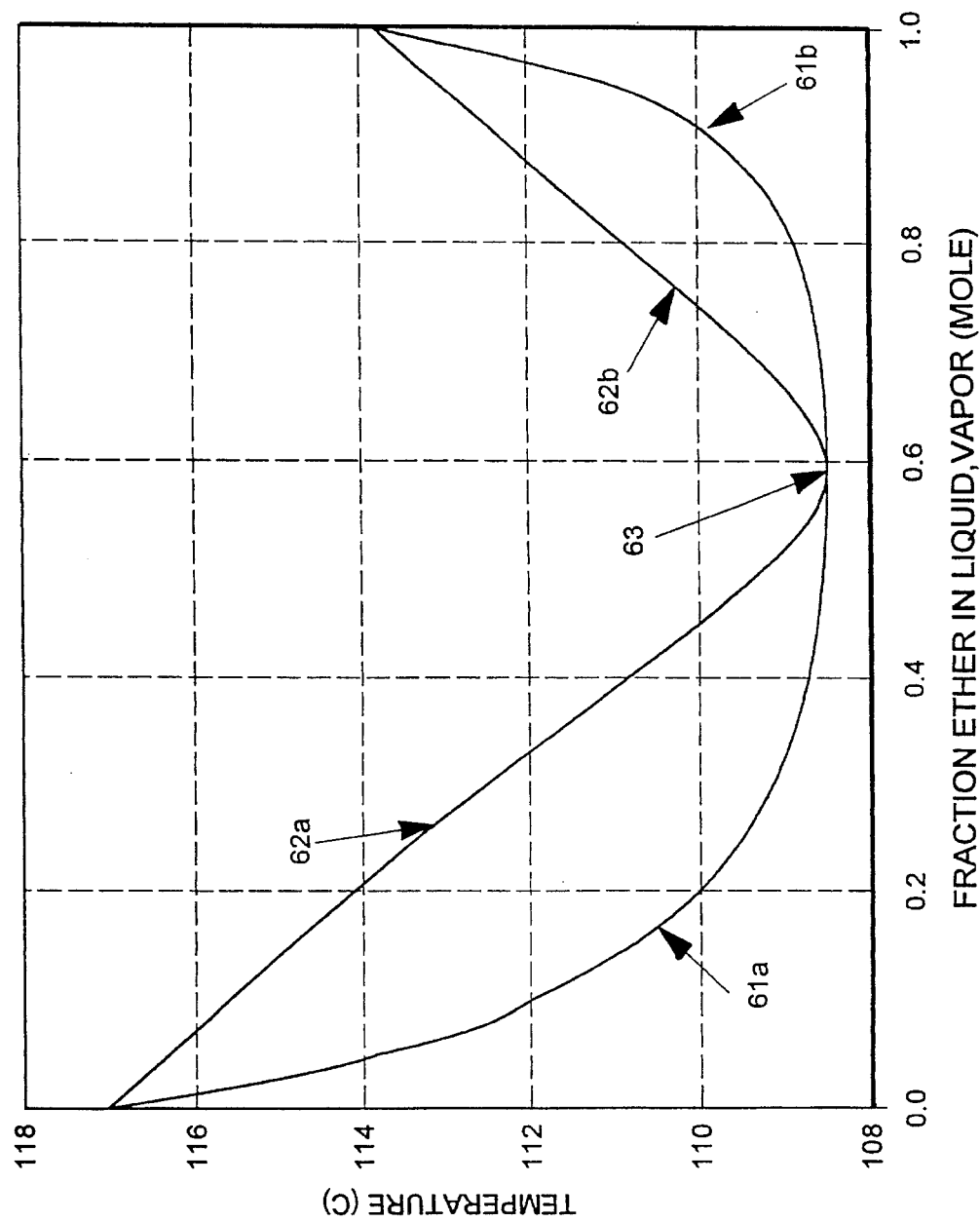

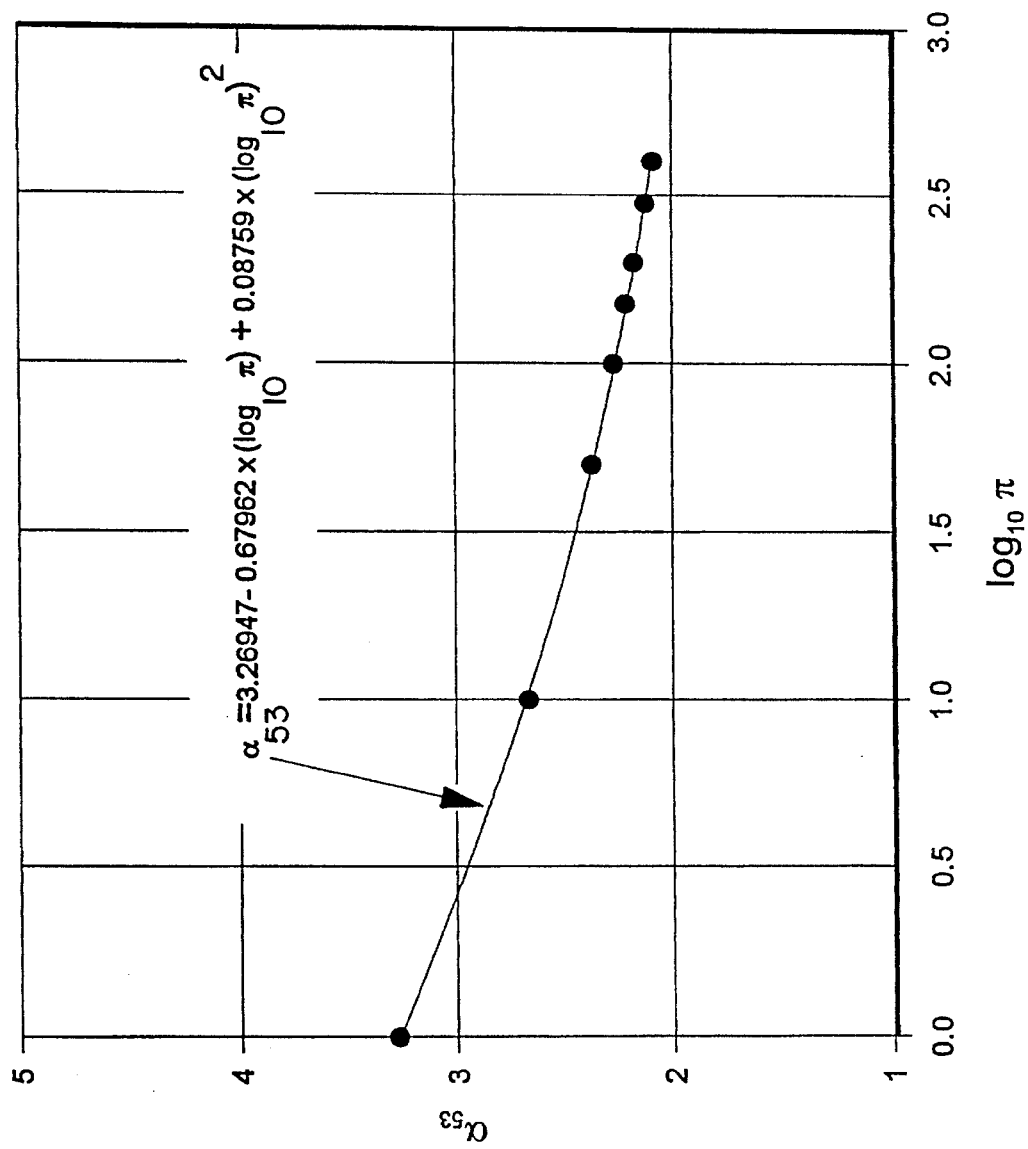

PROCESS FOR SEPARATION OF VANILLIN BY MEANS OF AZEOTROPIC DISTILLATION WITH DIBENZYL ETHER

BACKGROUND OF THE INVENTION

Vanilla is highly prized for use in flavoring a broad array of foodstuffs. Its use is restricted by high costs stemming from the complex, low yielding methods associated with its manufacture. Vanillin having the structure:

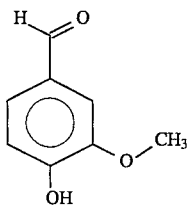

is one of the principal components responsible for the characteristic aroma and flavor of vanilla extract. Several processes for producing vanillin in combination with other materials which have boiling points close to that of vanillin are known, for example:

Labuda, et al, I, U.S. Letters Pat. No. 5,128,253 issued on Jul. 7, 1992; Title: "BIOCONVERSION PROCESS FOR THE PRODUCTION OF VANILLIN";

Labuda, et al, II, U.S. Letters Pat. No. 5,279,950 issued on Jan. 18, 1994; Title: "BIOCONVERSION PROCESS FOR THE PRODUCTION OF VANILLIN"; and Dolfini, et al, U.S. Letters Pat. No. 4,927,805 issued on May 22, 1990; Title: "HYDROLYSIS OF CURCUMIN".

Thus, many of these processes produce vanillin in combination with such materials as parahydroxybenzaldehyde having the structure:

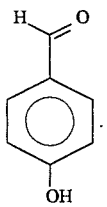

Vanillin, a solid with a melting point of 82° C., is a valuable ingredient. However, it is a difficult compound to distill from such mixtures. Not only is it a high boiling substance subject to decomposition, but it is also limited by the need to keep it liquid. This requires a relatively high (>1 mmHg) pressure and thus, temperature at which it must be distilled is high. The distillation is further complicated by its propensity to sublime. Distillation and vapor and vacuum lines are constantly subject to being clogged by the deposition of sublimed vanillin. Because of the relatively high temperatures at which vanillin has to be distilled, pot decomposition becomes a twofold problem.

Decomposition makes it difficult to maintain low pressure which leads to higher pot temperatures which, in turn, lead to even more decomposition. During the distillation procedure, the pot temperature typically starts out at 180° C. at 1–5 mmHg pressure when the vanillin begins to distill and the pot temperature rises to 220° C. or higher towards the end of the distillation with the pressure difficult to maintain below 20 mmHg.

Decomposition leads to polymerization and solidification of the pot contents. This makes it impossible to carry out commercial-size pot distillations (or "batch") distillations. Batch distillations run as such can only be accomplished in small (22 liter) glass stills which require strong caustic soap digestion with direct steam injection needed to clean the apparatus adequately. Glass pots can only be subjected to this procedure a few times before they fail in operation. Such decomposition also leads to off-odors and yellow color in the resulting vanillin product. Previously, intensive crystallization is required by practitioners in the art to reduce such off-odors and yellow color.

When vanillin is produced in combination with such materials as parahydroxybenzaldehyde, practitioners in the art have previously relied on multiple crystallization of vanillin to reduce the parahydroxybenzaldehyde and other chemicals to levels generally as low as 1% or even less. This leads to significant loss of the valuable vanillin.

Some of the aforesaid decomposition of the vanillin has been found by practitioners in the art to be avoided by utilizing thin-film evaporation to minimize the exposure to heat. However, this approach also has its attendant problems. A relatively non-volatile solvent is required and the sublimation as discussed, supra, gives rise to problems. Thus, with the running of a short path, wiped film evaporator, distillation capacity is limited by the high condenser temperatures since the vapor needed for condensation of vanillin as a liquid and sublimation lead to system breakdown fairly regularly. Additionally, any cold spots in the distillation lines lead to occasional line "freeze ups" which become difficult to isolate and remove.

Thus, we have discovered that the ideal co-distillate is to be a liquid at low temperature and reduces the temperature at which the vanillin can be distilled. The liquid co-distillate will thus act as a solvent for the vanillin to keep it from subliming and freezing out.

The thus-discovered co-distillate is dibenzyl ether having the structure:

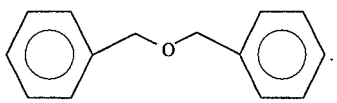

Prior art techniques have been developed for separation of co-reaction products from vanillin including separation of aldehydes from vanillin including *Chemical Abstracts*, Volume 107:108522p, Cela, et al, abstract of *Anal. Chim. Acta* 1986, Volume 191, pages 283–297 where a theoretical model is described for quick pre-optimization of binary multistep gradient elutions in liquid chromatography including separation of vanillin from various benzaldehyde derivatives.

In *Chemical Abstracts*, Volume 100:101716b, an azeotropic method for determination of weight loss and determination of moisture and content of vanillin and parahydroxybenzaldehyde in vanilla beans is disclosed.

Although mixtures of vanillin and dibenzyl ether along with many other materials are known, for example, Buil, et al, *parfums, cosmétiques, arômes*, No. 52, August–September 1983, pages 45–49, at page 46, nothing in the prior art shows mixtures consisting of vanillin and dibenzyl ether and thus, nothing in the prior art shows the use of dibenzyl ether as an azeotroping agent for separation of vanilla from other organic chemicals produced therewith, for example, Parahydroxybenzaldehyde.

Azeotropic distillations and data using as one of the components an organic ether are known in the literature.

Thus, Horsley, et al, "AZEOTROPIC DATA", published June 1952 by the AMERICAN CHEMICAL SOCIETY ("Advances in Chemistry Series") discloses a binary azeotrope formulation containing benzyl phenyl ether having the structure:

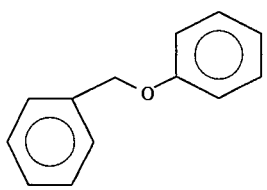

an α-toluic acid having the structure:

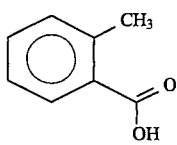

at page 218 and further discloses benzyl ether having the structure:

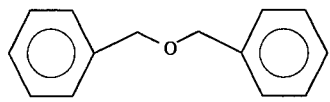

in combination with phenyl benzoate having the structure:

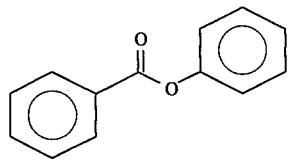

at page 249 (No. 14500) (as a "nonazeotrope"); and further discloses the combination of isoamyl salicylate having the structure:

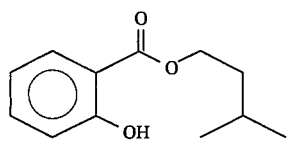

in combination with benzyl phenyl ether having the structure:

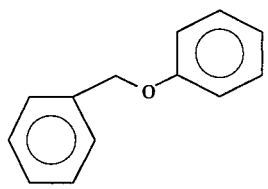

(No. 14493) (also indicated as a nonazeotrope). Such disclosure is considered to teach away from our invention.

Berg, I, U.S. Letters Pat. No. 5,382,329 issued on Jan. 17, 1995 discloses the separation of 1-decene from decane by azeotropic distillation using, inter alia, methyl, t-butyl ether as the azeotroping agent. Berg, II, U.S. Letters Pat. No. 5,382,330 issued on Jan. 17, 1995 discloses the separation of 1-octene from octane by azeotropic distillation using, inter alia, t-amyl methyl ether as the azeotroping agent.

Berg, III, U.S. Letters Pat. No. 5,401,366 issued on Mar. 28, 1995 discloses the separation of 1-butanol from 2-pentanol by means of extractive distillation using, inter alia, butyl ether as the "extractive" agent.

Nothing in the prior art including the aforementioned references implicitly or explicitly discloses our invention covering mixtures consisting of dibenzyl ether and vanillin and methods of separating vanillin from second organic chemicals produced therewith such as parahydroxybenzaldehyde using dibenzyl ether as an azeotroping agent. Furthermore, nothing in the prior art discloses the products produced by such methods.

THE INVENTION

We have discovered that dibenzyl ether having the structure:

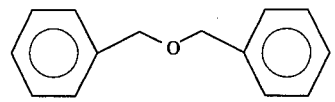

forms a minimum boiling azeotrope with vanillin having the structure:

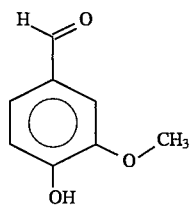

thus providing an improvement in the purification of vanillin and thus providing for the opportunity to provide a cost effective, highly pure form of vanillin.

More specifically, we have discovered a method for recovering vanillin having the structure:

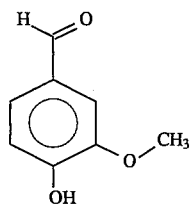

from a mixture of (i) vanillin and (ii) a second organic chemical forming a single liquid phase with said vanillin at a temperature of from 20° up to about 50° C. at one atmosphere of pressure which comprises:

(1) distilling a mixture of vanillin and said second organic chemical in the presence of an azeotrope forming agent which is dibenzyl ether having the structure:

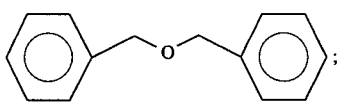

(2) recovering a single phase liquid mixture of vanillin and dibenzyl ether azeotroping agent as overhead product and said second organic chemical from the still pot (for example, parahydroxybenzaldehyde having the structure:

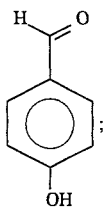

(3) separating said vanillin from said dibenzyl ether azeotrope forming agent by cooling said single phase mixture of vanillin and dibenzyl ether whereby vanillin crystals precipitate from said mixture of vanillin and dibenzyl ether; and (4) separating said vanillin crystals from said single phase mixture of vanillin and dibenzyl ether.

This method is particularly applicable where the second organic chemical is parahydroxybenzaldehyde.

This method is preferred wherein the step of recovering the single phase containing vanillin and dibenzyl ether as overhead distillation product takes place at a temperature of between about 108° C. and about 152° C. at a system pressure of from about 1 mmHg up to about 10 mmHg.

This method is also preferred wherein the step of recovering the single phase of vanillin and dibenzyl ether as overhead product takes place wherein the mole fraction of dibenzyl ether in the liquid phase and the vapor phase varies from about 0.42 up to about 0.53 at a system pressure of from about 1 mmHg up to about 200 mmHg.

Our invention also is intended to cover the products (crystalline vanillin having very small dibenzyl ether impurities) produced according to the processes defined, supra.

Coincidental with the carrying out of the foregoing processes are the actual mixtures of our invention consisting of vanillin having the structure:

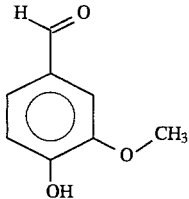

and dibenzyl ether having the structure:

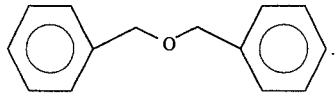

Such mixtures are intended to be a part of our invention.

The mixtures of vanillin and dibenzyl ether as part of our invention can be in the liquid phase or in the vapor phase; or such mixtures can be in the form of a vapor phase in equilibrium with a liquid phase.

The mixtures of vanillin and dibenzyl ether wherein the vapor phase is in equilibrium with the liquid phase contain mole fractions of dibenzyl ether in the liquid phase varying from about 0.16 up to about 0.80 and mole fractions of dibenzyl ether in the vapor phase varying from about 0.34 up to about 0.68 at system pressures of from about 1 mmHg up to about 200 mmHg.

Furthermore, the mixtures of vanillin and dibenzyl ether wherein the vapor phase is in equilibrium with the liquid phase of our invention have relative volatilities α defined according to the relationship:

$$\alpha = \left[ \frac{Y_v X_{DBE}}{Y_{DBE} X_v} \right]$$

varying from about 2.15 up to about 3.30 at a system pressure of from about 1 mmHg up to about 200 mmHg wherein $Y_V$ is the mole fraction of vanillin in the vapor phase; $X_V$ is the mole fraction of vanillin in the liquid phase; $Y_{DBE}$ is the mole fraction of dibenzyl ether in the vapor phase and $X_{DBE}$ is the mole fraction of dibenzyl ether in the liquid phase.

More particularly, dibenzyl ether having the structure:

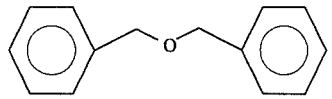

provides in the vanillin-second chemical-dibenzyl ether system many benefits:

(1) As a still base, dibenzyl ether causes dissolution of the crude vanillin in the various reaction products without dissolving the residue. Hence, the solid residue can be filtered away leading to an overall cleaner distillation;

(2) Since dibenzyl is an azeotroping co-distillate, the pot temperature during distillation remains relatively low: less than 170° C. at 7–8 mmHg throughout the distillation versus 210° C. or higher if a batch distillation is attempted to be carried out using vegetable oil as a still base or 190°–210° C. if other azeotroping agents (also newly discovered) are attempted to be used (FIGS. 3 and 4 described, infra, show that phenyl benzoate and vanillin form a maximum boiling azeotrope and FIG. 4 described, infra, illustrates likewise the formation of a maximum boiling azeotrope for phenyl ethyl benzoate) as co-distillates;

(3) Although dibenzyl ether azeotropes with such by-products resulting from forming vanillin as p-hydroxybenzaldehyde (pHB), significant differences between the azeotrope temperatures allow separation of such materials as parahydroxybenzaldehyde from the vanillin;

(4) Using dibenzyl ether as the azeotroping agent, continuous distillations are conveniently carried out. Thus, for example, with an average composition of 88% vanillin and 12% parahydroxybenzaldehyde, one can predict that the respective distillate composition would be 98.5:1.5 and the bottoms would be 65:35 (vanillin:parahydroxybenzaldehyde) for a single pass through a 10-plate column. Recycling allows recovery of most of the vanillin;

(5) As a co-distillate, dibenzyl ether prevents vanillin from subliming. Sublimation is problematical because the redeposited crystals plug distillate and vacuum lines and other equipment;

(6) As a co-condensate, dibenzyl ether solvolizes the vanillin thereby minimizing line blockage; and (7) Vanillin is minimally soluble at cold temperatures in dibenzyl ether and dibenzyl ether is a liquid to 1° C.; thus we have been able to determine that vanillin readily crystallizes from dibenzyl ether:
  (a) after simple hexane washing of the crystals, the residual dibenzyl ether is less than 0.2%; and
  (b) if refluxed in hexane, the dibenzyl ether ends up at a trace level in the final vanillin product.

FIG. 5 described, infra, shows the vapor-liquid equilibria for the vanillin-dibenzyl ether combination at several system pressures. This combination forms a minimum boiling azeotrope which is largely unaffected by system pressure. The T-X-Y (temperature-liquid mole fraction-vapor mole fraction) diagrams (FIGS. 6 and 7 described, infra) at 1 and 10 mmHg show that distillation temperatures can be significantly reduced. Because of the azeotrope existence, distillations can be set up so that a constant composition of the distillate is maintained. While the second chemical such as parahydroxybenzaldehyde forms a similar azeotrope (FIG. 8 described, infra), the reduction of temperature and the physical properties of the dibenzyl ether allows for reflux with minimum decomposition of the vanillin. Thus, the second chemical such as parahydroxybenzaldehyde is able to be separated from the vanillin. FIG. 9 described, infra, shows a continuous distillation setup. Dibenzyl ether has the added benefits of being a GRAS substance and of having a low odor.

The behavior of the two components, the vanillin in combination with the dibenzyl ether, is described by the Wilson equation, to wit:

$$\ln(\gamma_{[1]}) = -\ln(x_{[1]} + A_{[1,2]}x_{[2]}) + x_{[2]}\left(\frac{A_{[1,2]}}{x_{[1]} + A_{[1,2]}x_{[2]}} - \frac{A_{[2,1]}}{A_{[2,1]}x_{[1]} + x_{[2]}}\right)$$

and $$\ln(\gamma_{[2]}) = -\ln(A_{[1,2]} + x_{[1]} + x_{[2]}) - x_{[1]}\left(\frac{A_{[1,2]}}{x_{[1]} + A_{[1,2]}x_{[2]}} - \frac{A_{[2,1]}}{A_{[2,1]}x_{[1]} + x_{[2]}}\right)$$

as further defined by the equations:

$$Y_{[1]}P = X_{[1]}\gamma_{[1]}P_{[1]}^{SAT}$$

and $$Y_{[2]}P = X_{[2]}\gamma_{[2]}P_{[2]}^{SAT}$$

wherein the symbol, $\gamma_{[1]}$, is the activity coefficient of vanillin; the symbol, $\gamma_{[2]}$, is the activity coefficient for dibenzyl ether; the symbol, $X_{[1]}$, represents the mole fraction of vanillin in the liquid phase; the symbol, $X_{[2]}$, is the mole fraction in the liquid phase for dibenzyl ether; the symbol, $Y_{[1]}$, is the mole fraction for vanillin in the vapor phase; the symbol, $Y_{[2]}$, is the mole fraction of dibenzyl ether in the vapor phase; the symbol, $A_{[1,2]}$, is the Wilson coefficient for vanillin with respect to dibenzyl ether and is 676.5598; and the symbol, $A_{[2,1]}$, is the symbol for the Wilson coefficient for dibenzyl ether with respect to vanillin and is 212.0837. The symbol, $P_{[1]}^{SAT}$, is the vanillin vapor pressure at system temperature. The symbol, $P_{[2]}^{SAT}$, is the dibenzyl ether pure component vapor pressure at system temperature. The symbol, P, also shown by the symbol, Π, is the system pressure.

The references more particularly describing the aforementioned Wilson equation and the meaning of the Wilson coefficients are as follows:

Holmes, et al, *INDUSTRIAL AND ENGINEERING CHEMISTRY*, Volume 62 (1) January 1970, pages 21–31;

Orye, et al, *INDUSTRIAL AND ENGINEERING CHEMISTRY*, Volume 57 (5) May 1965, pages 18–26; and Wilson, *Journal of the American Chemical Society*, Volume 86, pages 127–130.

Our invention can also be practiced via a batch distillation as shown in FIG. 12 (described, infra). We found that while maintaining pressures between 5 and 15 mmHg, the pot temperature is capable of being maintained below 170° C. with (1) low decomposition; (2) little color being in the distillate; and (3) a lack of the typical smoky notes of decomposition. The resulting distillate is easily kept liquid during the distillation and there is no sublimation to contend with. After evolution from the distillation column, the vanillin is directly crystallized out of the benzyl ether. The crystals after washing with hexane contain less than 0.2% dibenzyl ether and about 0.25% second organic chemical such as parahydroxybenzaldehyde. These directly formed crystals are found to be organoleptically acceptable. If the crystals are then worked up by means of refluxing in hexane, the dibenzyl ether is reduced to a trace level.

BRIEF DESCRIPTION OF THE DRAWINGS

FIG. 6 is a temperature-mole fraction in liquid-mole fraction in vapor equilibrium diagram for the binary mixture of dibenzyl ether and vanillin at 1 mmHg pressure showing a minimum azeotrope point.

FIG. 11 is a graph showing relative volatility (α) versus +log₁₀Π wherein the relative volatility is at a mole fraction of dibenzyl ether in the liquid phase of 0.8 and is measured from the line indicated by reference numeral 54 in FIG. 5.

$$\alpha_{54} = 0.4767 - 0.5669 \, (\log_{10}\Pi) + 0.01485 \, (\log_{10}\Pi)^2.$$

Figure 12:
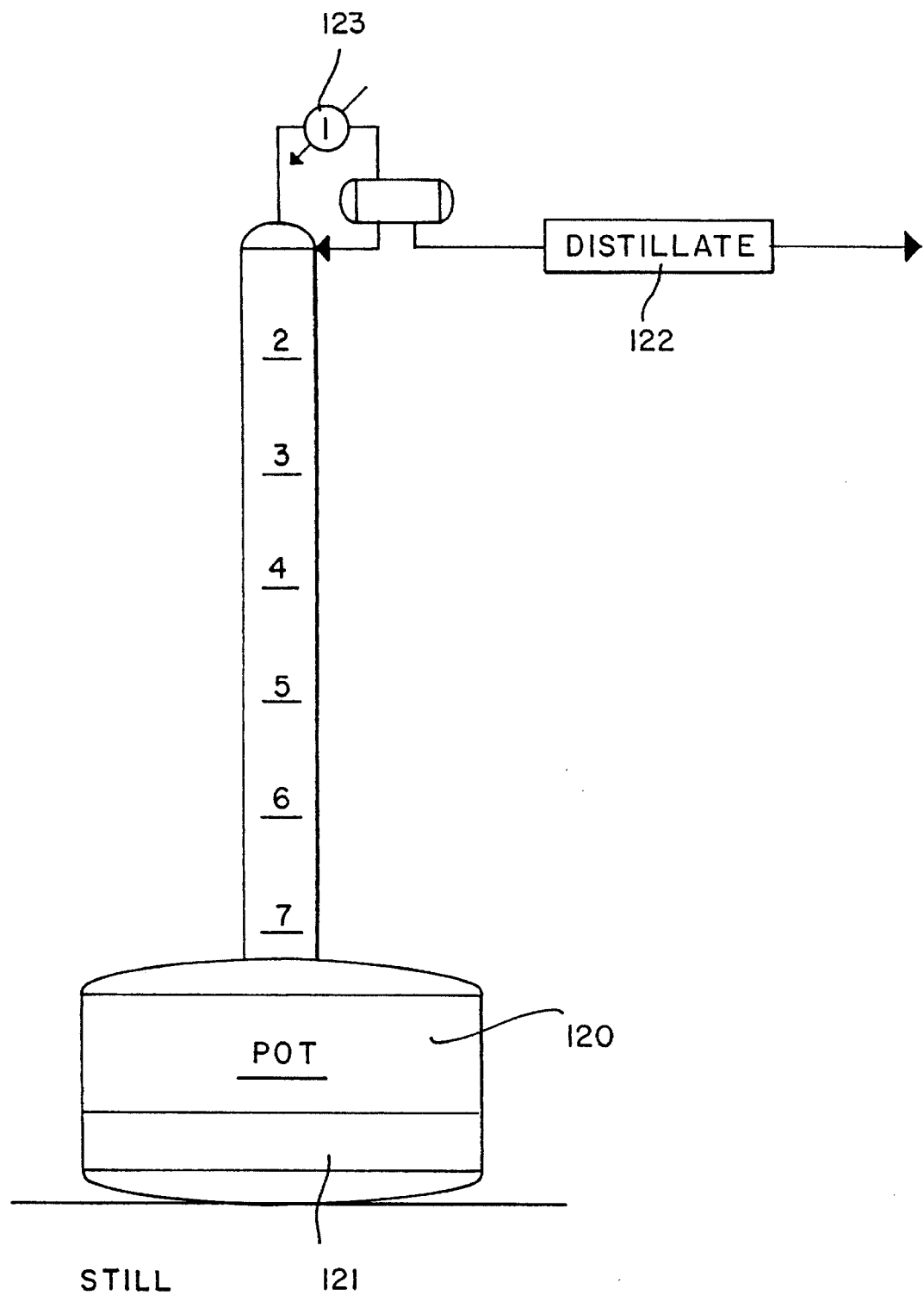

FIG. 12 is a schematic diagram of a batch distillation process using the procedure of Example I set forth, infra, and showing 7 "plates" including the reflux "plate".

DETAILED DESCRIPTION OF THE DRAWINGS

Figure 1:
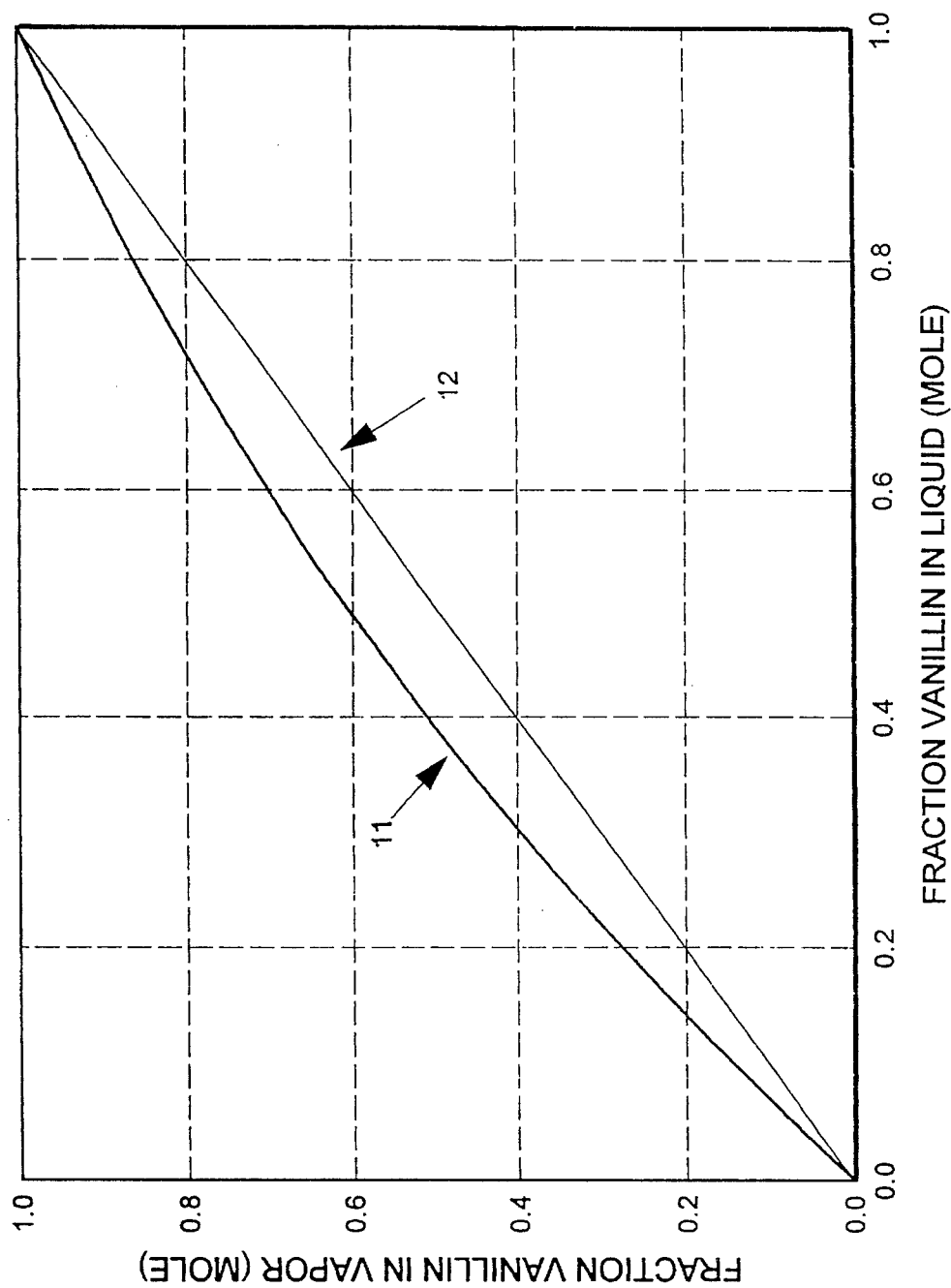
FIG. 1 is a vapor-liquid equilibrium diagram for the binary mixture of vanillin and parahydroxybenzaldehyde at 10 mmHg system pressure.

In FIG. 1, the curve indicated by reference numeral 11 is for the fraction of vanillin in the vapor phase in equilibrium with the liquid phase which is shown by reference numeral 12 which indicates the fraction of vanillin in the liquid phase.

Figure 2:
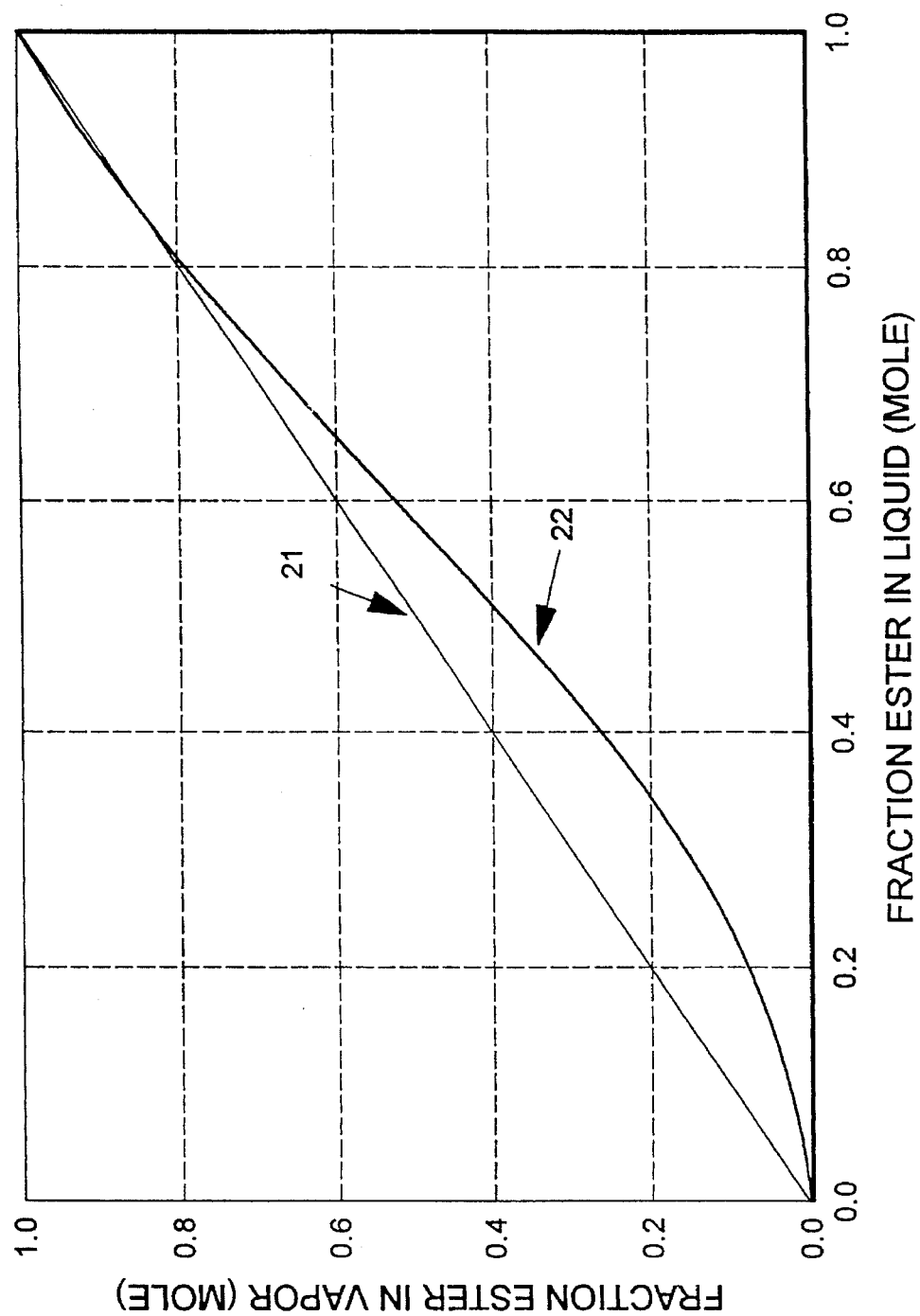
FIG. 2 is a vapor-liquid equilibrium diagram for the binary mixture of phenyl benzoate and vanillin at 1 mmHg pressure.

In FIG. 2, the graph indicated by reference numeral 21 is for the fraction of phenyl benzoate in the liquid phase and the graph indicated by reference numeral 22 is for the fraction of phenyl benzoate in the vapor phase.

Figure 3:
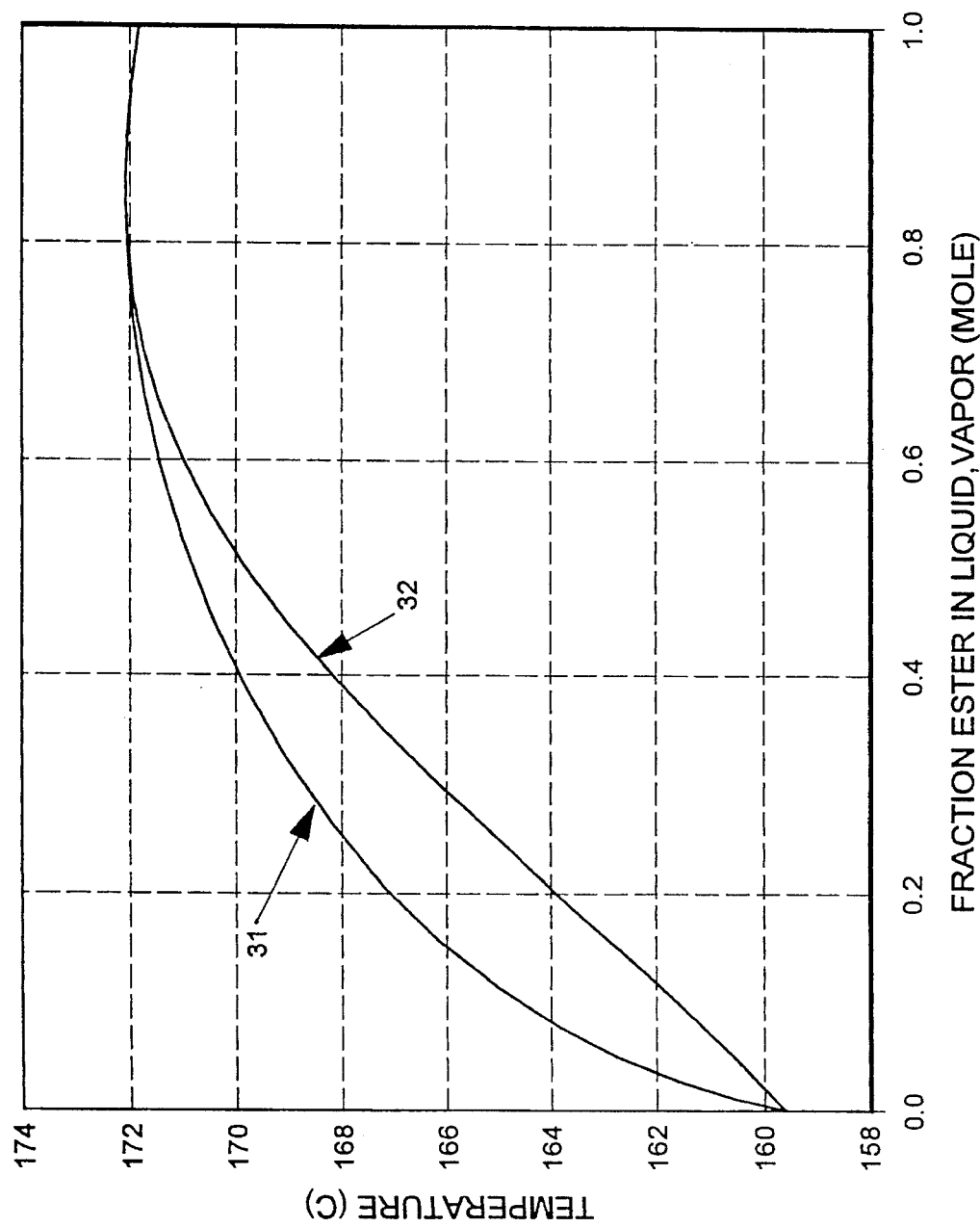
FIG. 3 is a temperature-mole fraction in liquid-mole fraction in vapor equilibrium diagram for the binary mixture of phenyl benzoate and vanillin at 1 mmHg pressure.

In FIG. 3, the graph indicated by reference numeral 31 is for the fraction of phenyl benzoate in the vapor phase and the graph indicated by reference numeral 32 is the fraction of phenyl benzoate in the liquid phase, both versus temperature.

Figure 4:
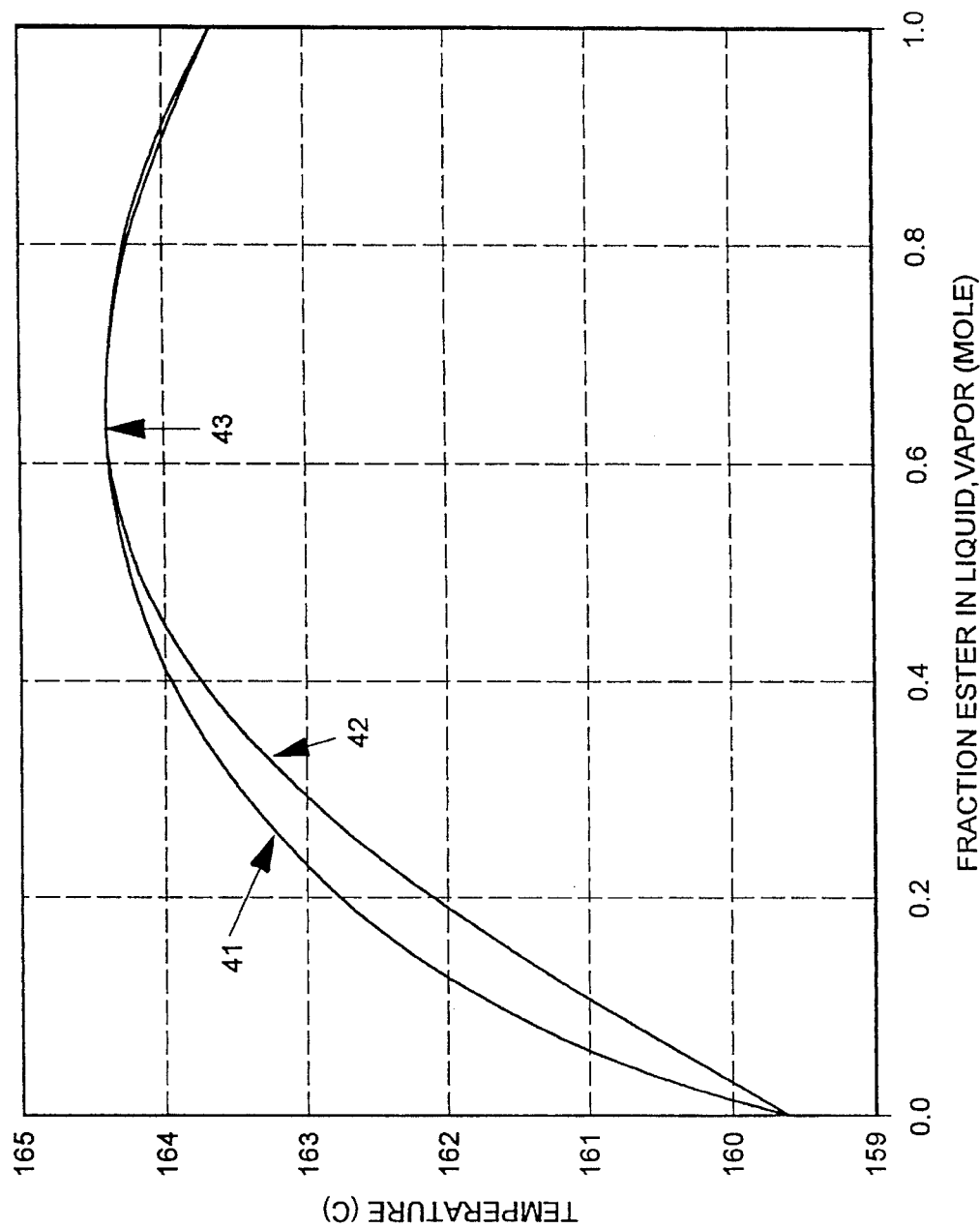
FIG. 4 is a temperature-mole fraction in liquid-mole fraction in vapor equilibrium diagram for the binary mixture of phenyl ethyl benzoate and vanillin at 10 mmHg pressure showing a maximum azeotrope point.

In FIG. 4, the point indicated by reference numeral 43 is for the maximum azeotrope at about 164.3° C. for the binary mixture, phenyl ethyl benzoate and vanillin. The graph indicated by reference numeral 41 is for the mole fraction of phenyl ethyl benzoate in the vapor phase versus temperature at 10 mmHg. The graph indicated by reference numeral 42 is for the mole fraction of phenyl ethyl benzoate in the liquid phase in equilibrium with the vapor phase at 10 mmHg versus temperature.

Figure 5:
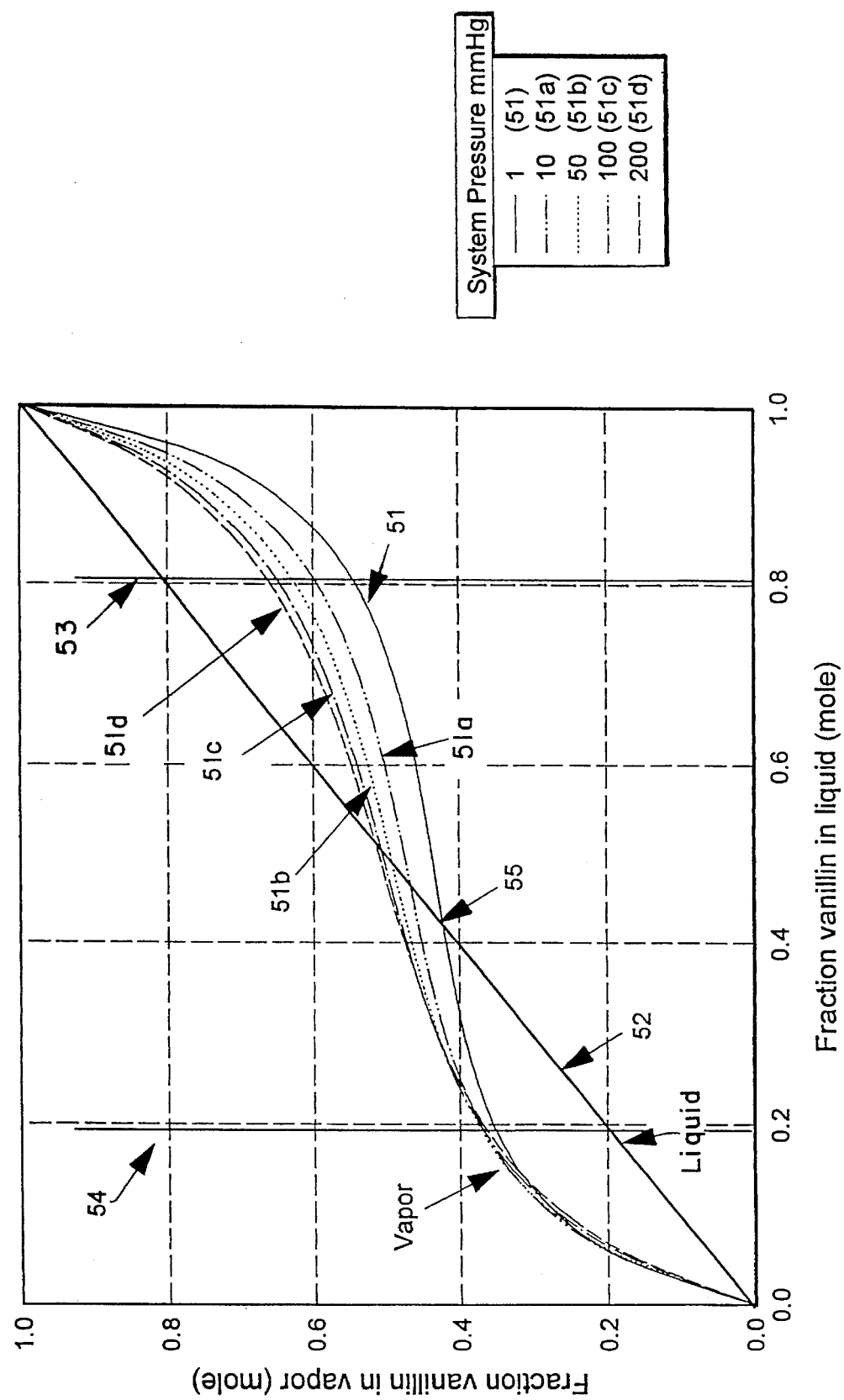
FIG. 5 is a vapor-liquid equilibrium diagram for various system pressures from 1 up to 200 mmHg for the binary mixture of vanillin and dibenzyl ether.
Figure 5A:
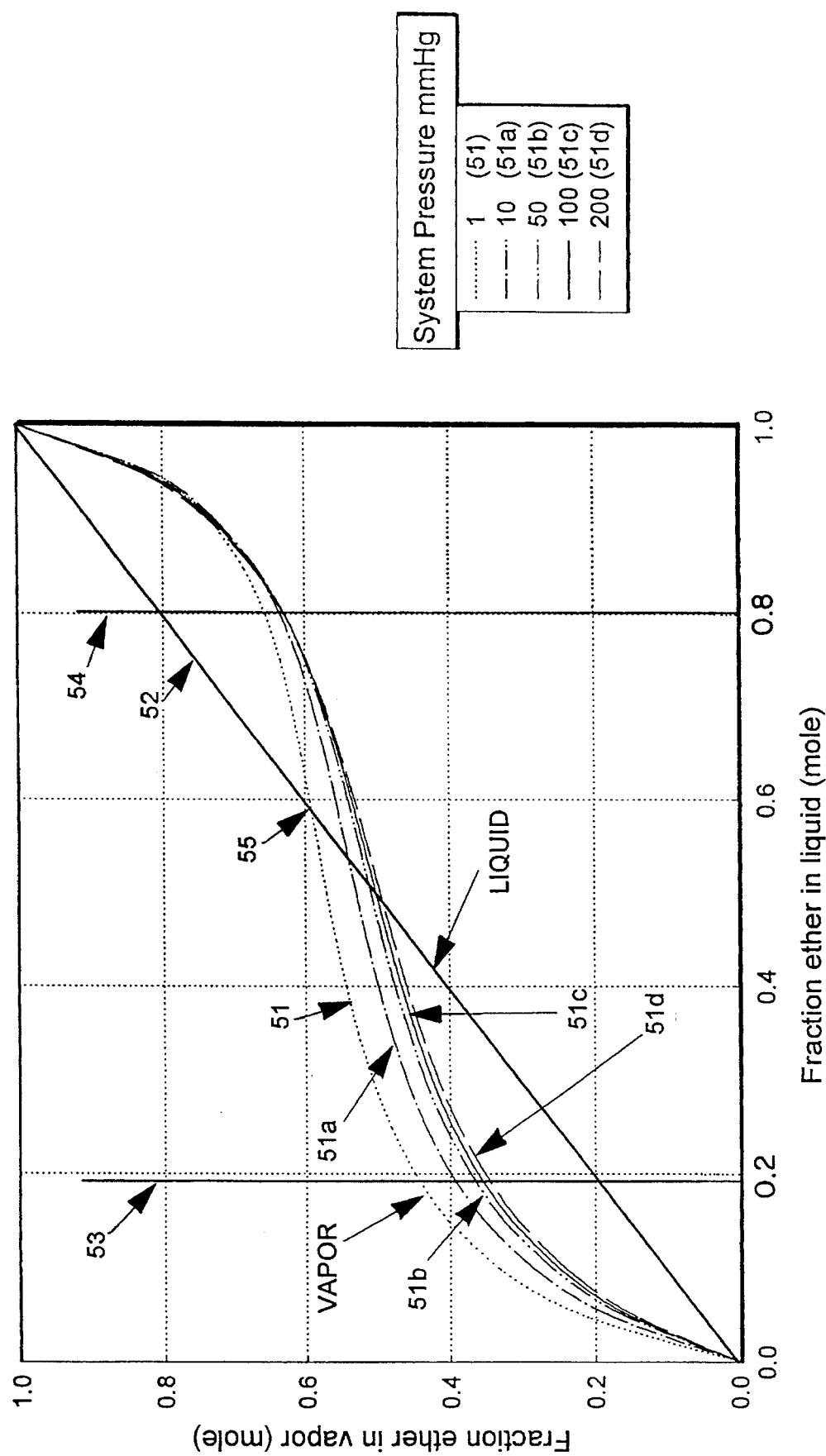
FIG. 5A is a graph of the mole fraction of dibenzyl ether in the vapor phase versus the mole fraction of dibenzyl ether in the liquid at system pressures of 1 mmHg, 10 mmHg, 50 mmHg, 100 mmHg and 200 mmHg. The graph is for the binary mixture, dibenzyl ether and vanillin, showing an equilibrium curve for the vapor phase and an operating line for the liquid phase wherein at the intersection thereof at the azeotrope point, the operating liquid line meets the vapor-liquid equilibrium line.

In FIG. 5, the graph indicated by reference numeral 52 is for the mole fraction of dibenzyl ether in the liquid phase in equilibrium with the dibenzyl ether in the vapor phase. The graph indicated by reference numeral 51 is for the mole fraction of dibenzyl ether in the vapor phase in equilibrium with the dibenzyl ether in the liquid phase at 1 mmHg pressure. The graph indicated by reference numeral 51a is for the mole fraction of dibenzyl ether in the vapor phase in equilibrium with the dibenzyl ether in the liquid phase at 10 mmHg pressure. The graph indicated by reference numeral 51b is for the mole fraction of dibenzyl ether in the vapor phase in equilibrium with the dibenzyl ether in the liquid phase at 50 mmHg pressure. The graph indicated by reference numeral 51c is for the mole fraction of dibenzyl ether in the vapor phase in equilibrium with the dibenzyl ether in the liquid phase at 100 mmHg pressure. The graph indicated by reference numeral 51d is for the mole fraction of dibenzyl ether in the vapor phase in equilibrium with the dibenzyl ether in the liquid phase at 200 mmHg pressure. Each of the graphs is for the binary mixture of vanillin and dibenzyl ether. The point indicated by reference numeral 55 is the point indicating the azeotrope of vanillin and dibenzyl ether at 1 mmHg system pressure. The vertical line indicated by reference numeral 53 is the lower bound of the mole fraction of dibenzyl ether (vapor or liquid) and the line indicated by reference numeral 54 is the upper bound for the dibenzyl ether in the liquid and vapor phase for the composition of our invention, to wit: vanillin and dibenzyl ether, workable between 1 mmHg and 200 mmHg whereby azeotropic compositions are formed as distillates from batch and continuous distillation columns, from 1 up to 200 mmHg system pressure.

Referring to FIG. 6, the graphs indicated by reference numerals 61a and 61b are for the mole fractions of dibenzyl ether in the liquid phase versus temperature for the binary mixture of dibenzyl ether and vanillin at 1 mmHg. The graphs indicated by reference numerals 62a and 62b are for the mole fractions of dibenzyl ether in the vapor phase in equilibrium with the liquid phase at 1 mmHg pressure for the binary mixture of dibenzyl ether and vanillin. The point indicated by reference numeral 63 is the azeotrope point for the binary mixture of dibenzyl ether and vanillin at 1 mmHg, namely approximately 108.5° C. and at a mole fraction of dibenzyl ether of about 0.59.

Figure 7:
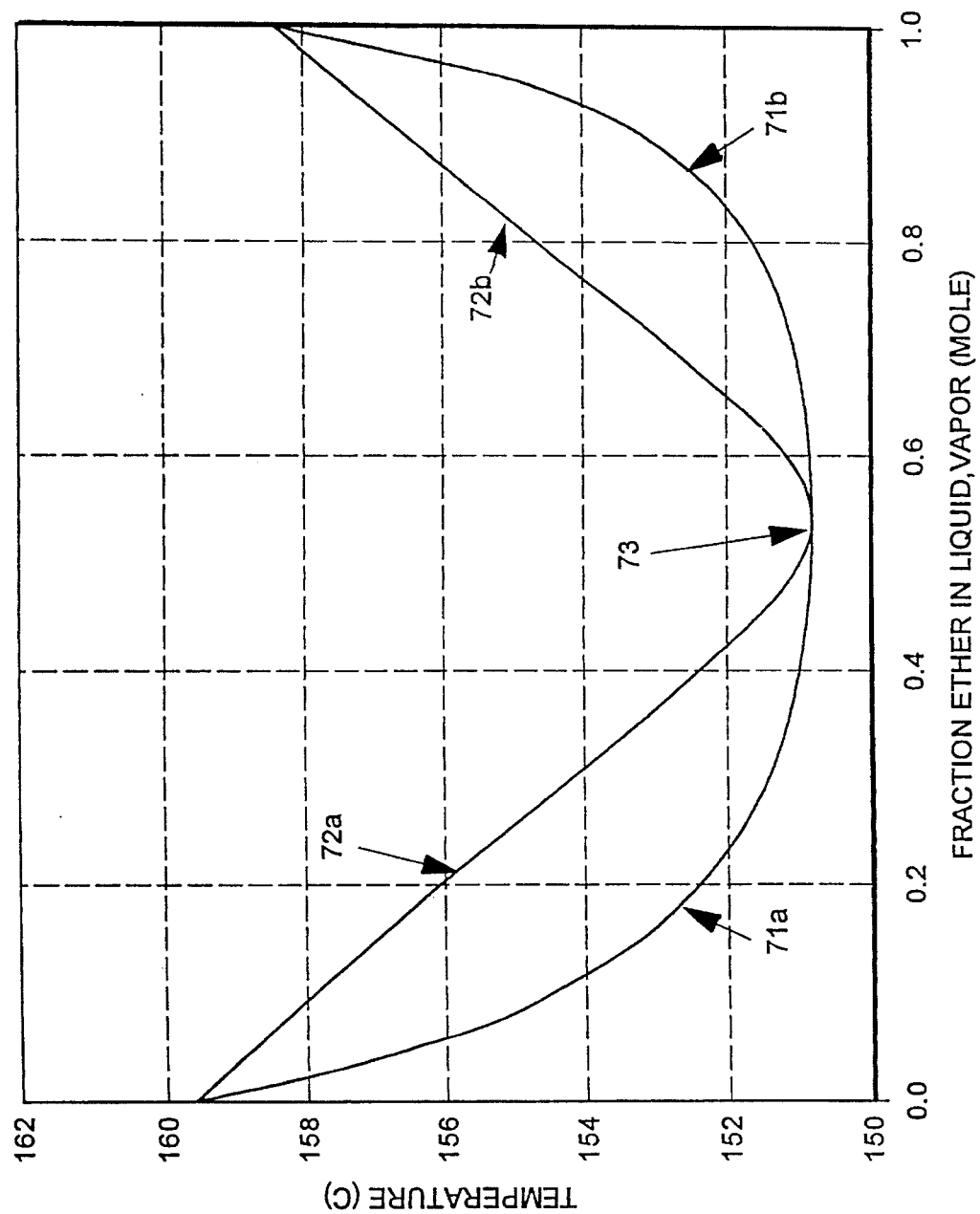
FIG. 7 is a temperature-mole fraction in liquid-mole fraction in vapor equilibrium diagram for the binary mixture of dibenzyl ether and vanillin at 10 mmHg pressure showing a minimum azeotrope point.

Referring to FIG. 7, the graphs indicated by reference numerals 71a and 71b are for the mole fractions of dibenzyl ether in the liquid phase in equilibrium with the vapor phase versus temperature at 10 mmHg pressure for the binary mixture of dibenzyl ether and vanillin. The graphs indicated by reference numerals 72a and 72b are for the mole fractions of dibenzyl ether in the vapor phase in equilibrium with the liquid phase versus temperature (°C.) at 10 mmHg pressure. The point indicated by reference numeral 73 is the azeotrope point for the binary mixture of dibenzyl ether and vanillin at 10 mmHg, namely at about 150.8° C. and at about 0.55 mole fraction of dibenzyl ether (in both the vapor and the liquid phase).

Figure 8:
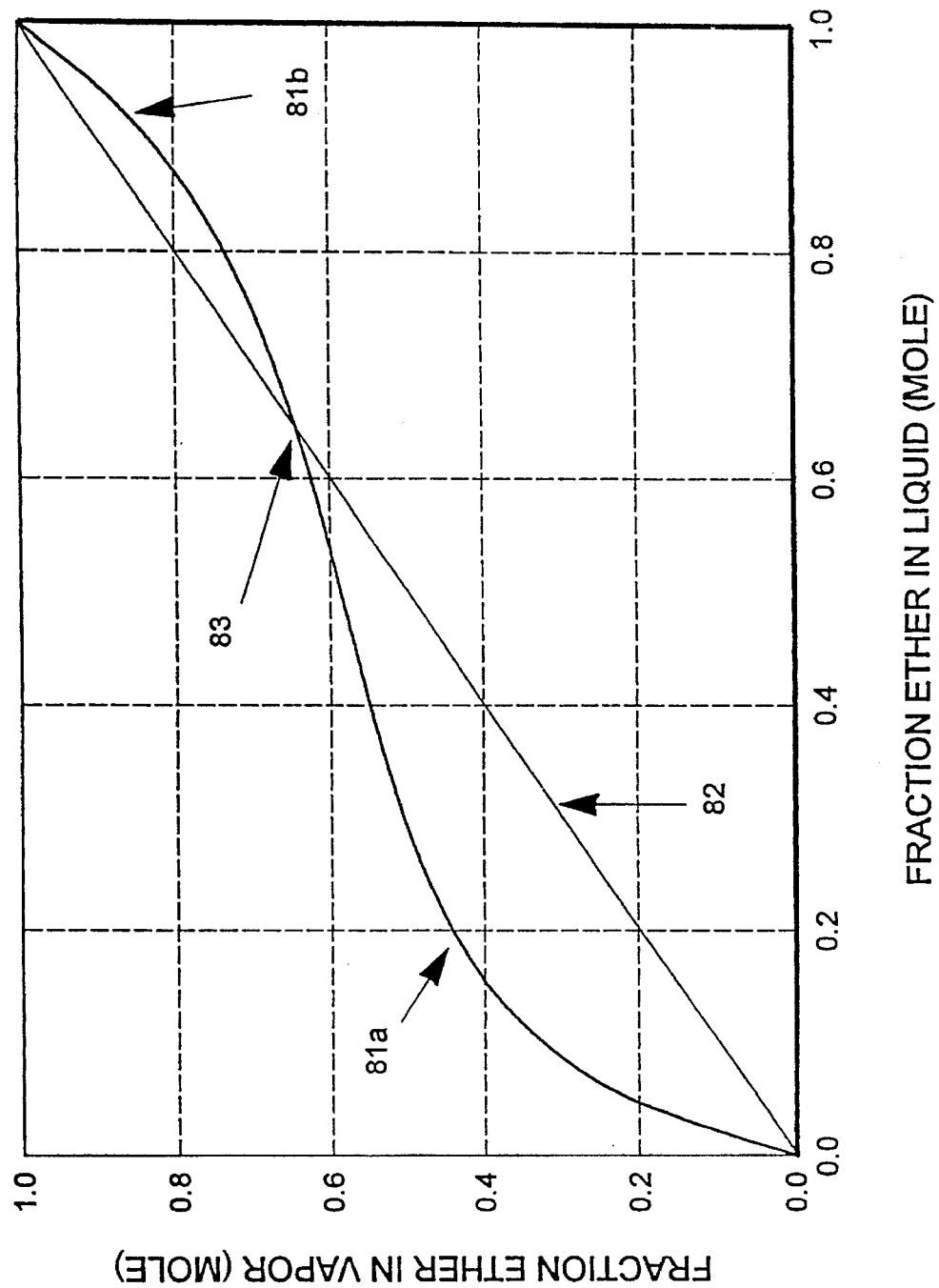
FIG. 8 is a vapor-liquid equilibrium diagram for the binary mixture of dibenzyl ether and parahydroxybenzaldehyde at 1 mmHg.

Referring to FIG. 8, FIG. 8 shows a vapor-liquid equilibrium diagram for dibenzyl ether at 1 mmHg for the binary mixture of dibenzyl ether and parahydroxybenzaldehyde. The graphs indicated by reference numerals 81a and 81b are for the mole fraction of dibenzyl ether in the vapor phase versus dibenzyl ether in the liquid phase at 1 mmHg pressure. The graph indicated by reference numeral 82 is the graph showing the mole fraction of dibenzyl ether in the liquid phase in equilibrium with the dibenzyl ether in the vapor phase at 1 mmHg pressure. The point indicated by reference numeral 83 is the azeotrope point for the binary mixture of dibenzyl ether and parahydroxybenzaldehyde, namely at about 0.7 mole fraction dibenzyl ether (in the liquid and vapor phase).

Figure 9:
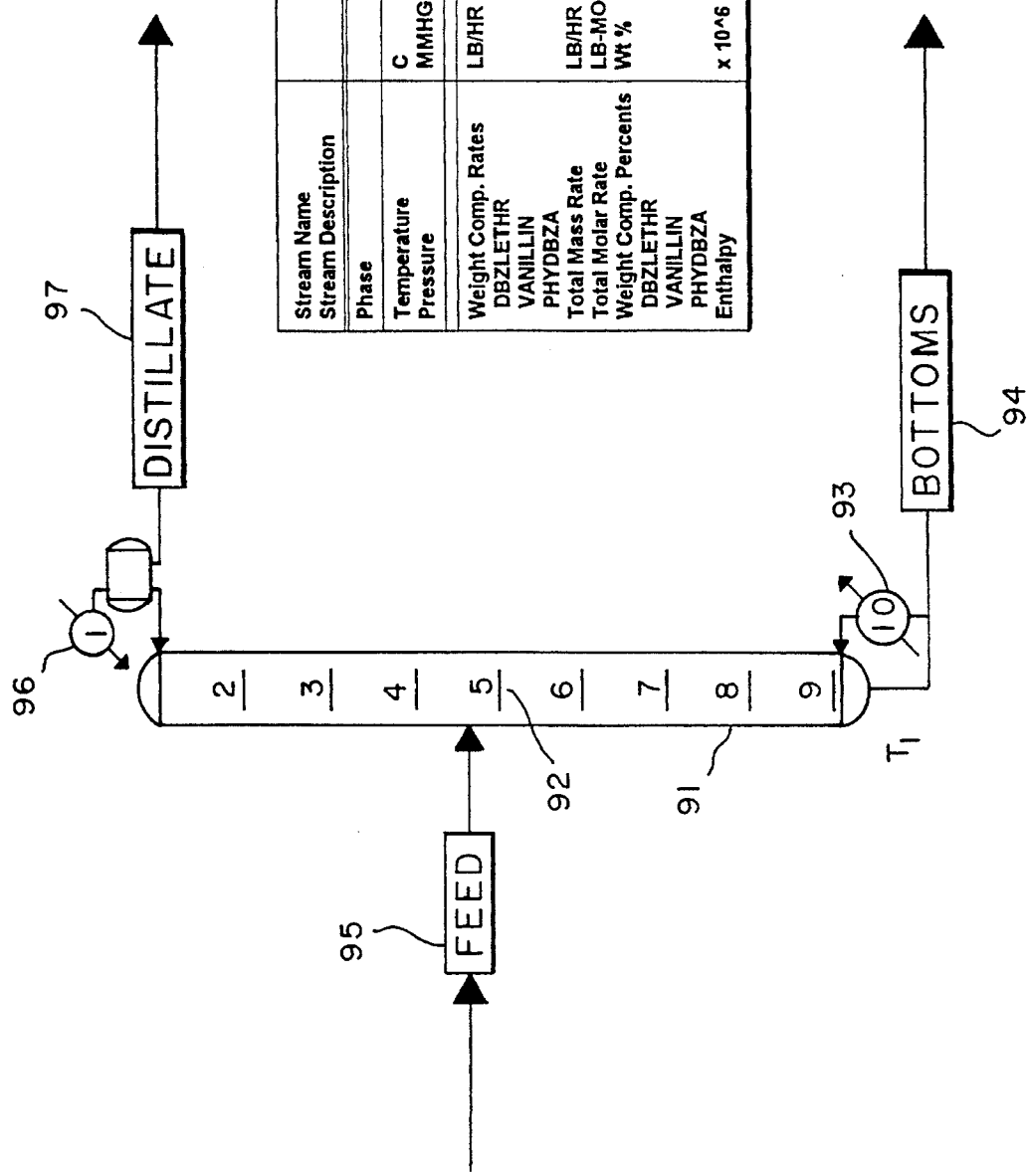
FIG. 9 is a schematic diagram of a continuous distillation operation for continuously distilling mixtures of vanillin, dibenzyl ether and parahydroxybenzaldehyde and is accompanied by a data table showing mole fractions of the three components in feed, distillate and bottoms for a 9-plate column (including reflux head).

Referring to FIG. 9, the diagram of the continuous distillation operation for separating parahydroxybenzaldehyde from vanillin using a dibenzyl ether azeotroping agent, the distillation column is indicated by reference numeral 91 and the feed plate is indicated by reference numeral 92. The bottoms recycle plate is indicated by reference numeral 93 and the bottoms collection container is indicated by reference numeral 94. The feed line is indicated by reference numeral 95, the reflux "plate" is indicated by reference numeral 96 and the distillation collection container is indicated by reference numeral 97. Reflux ratios vary from about 1:1 up to about 10:1.

Figure 10:
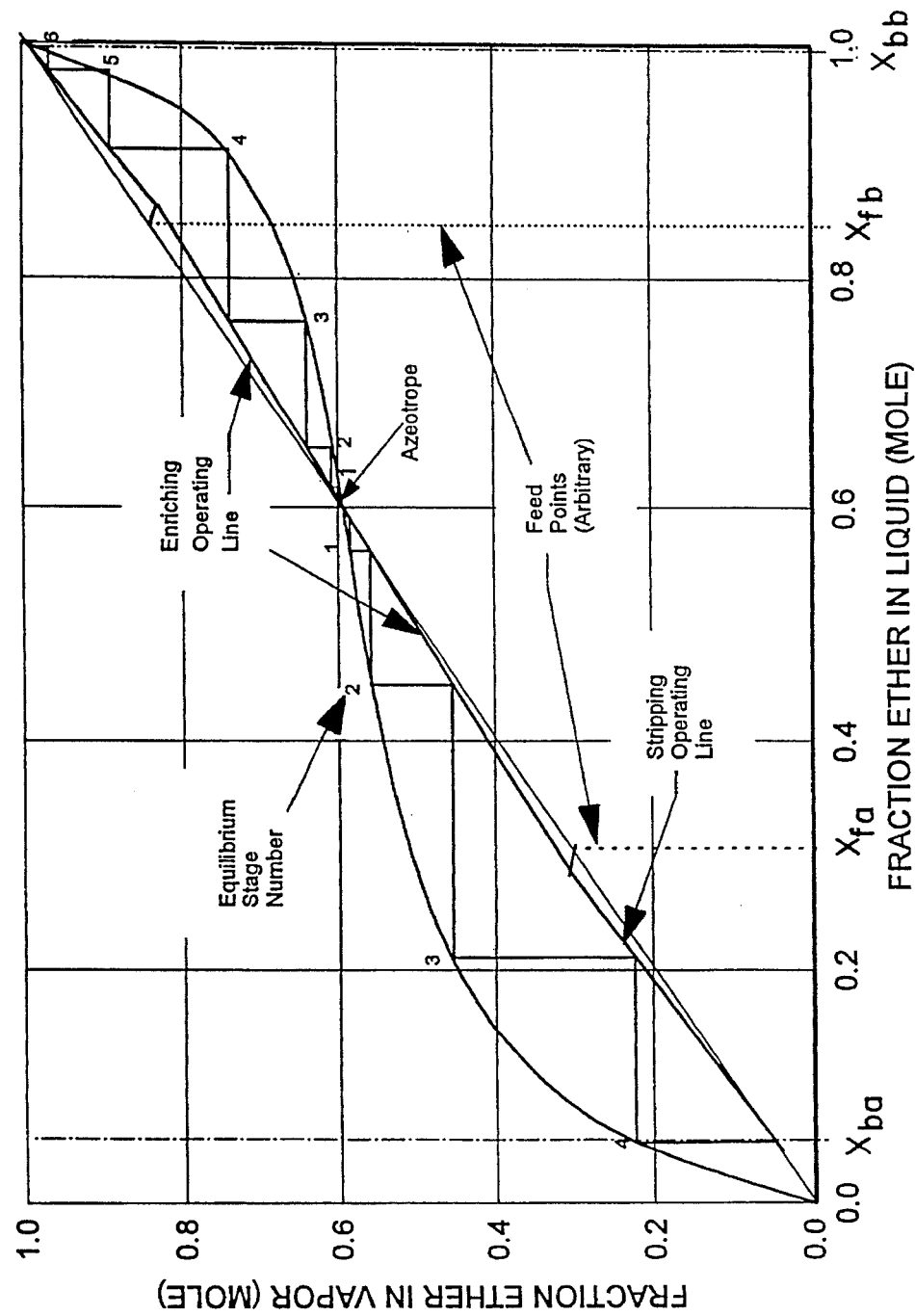
FIG. 10 is a McCabe-Thiele vapor liquid equilibrium diagram showing calculation of distillation plates for the binary mixture of dibenzyl ether and vanillin at 1 mmHg pressure.

Referring to FIG. 10, the McCabe-Thiele diagram for the binary mixture of dibenzyl ether and vanillin at 1 mmHg, the symbol, $X_{fa}$, is the feed composition at a point below the azeotrope; the symbol, $X_{ba}$, is the bottoms composition if the feed $X_{fa}$ is used; the symbol, $X_{fb}$, is the feed composition at a point above the azeotrope; and the symbol, $X_{bb}$, is the bottoms composition if the feed $X_{fb}$ is used; with the enriching operating lines being calculated at a reflux ratio of 10:1. Two feed points are shown to illustrate that whatever the feed composition is, the distillate concentration will move towards the azeotrope point.

Figure 11A:
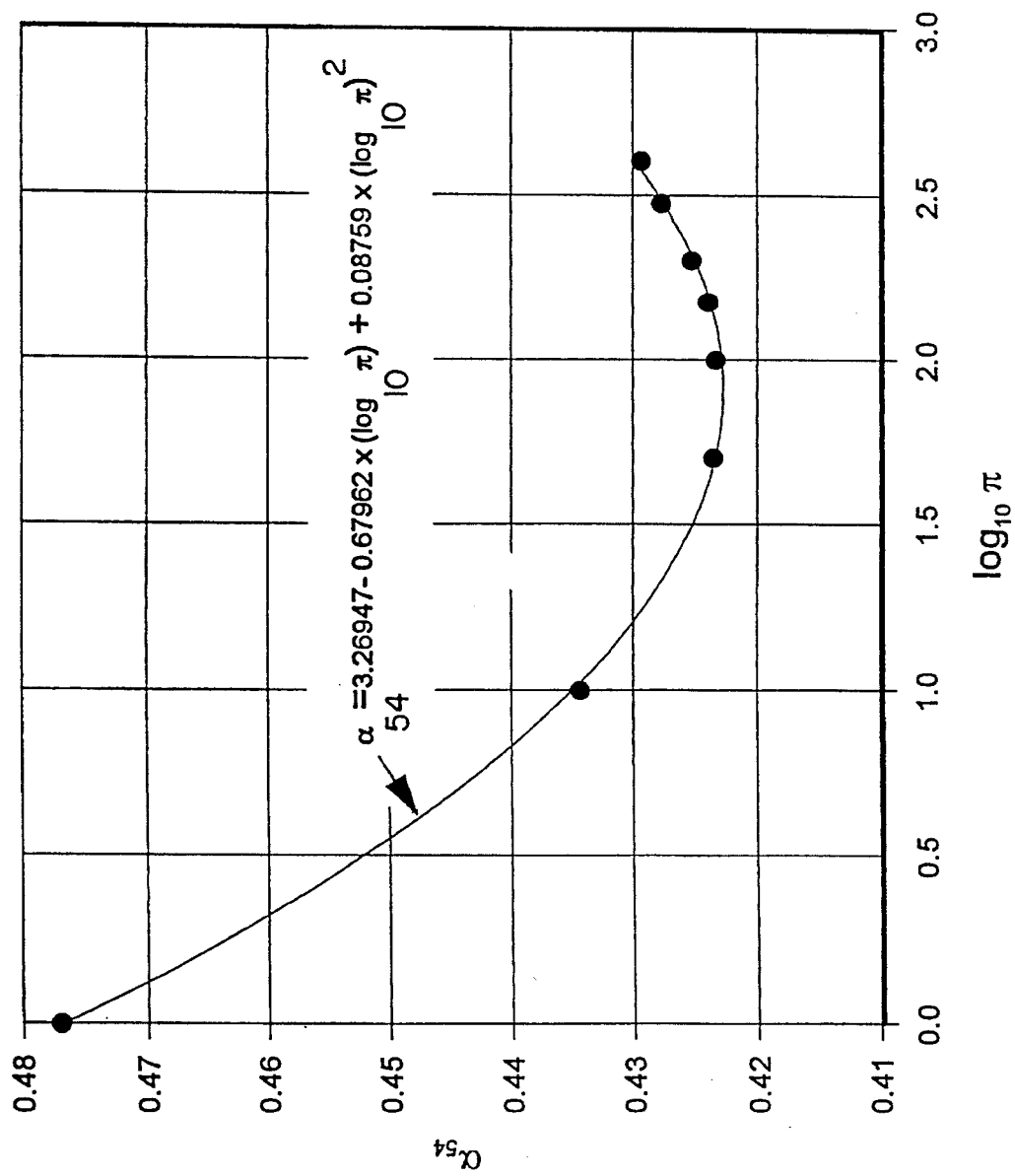
FIG. 11A is a graph of relative volatility (on the "Y" axis, $\alpha_{54}$) versus $\log_{10}\Pi$ on the "X" axis for the mixture, dibenzyl ether and vanillin, wherein the mole fraction of dibenzyl ether in the liquid phase is 0.8. The equation for FIG. 11A is a parabolic equation, to wit.

FIG. 11 is a graph of the $\log_{10}$ of system pressure indicated by the symbol: $+\log_{10}\Pi$ versus the relative volatility at the line indicated by reference numeral 54 on FIG. 5 at a mole fraction of dibenzyl ether in the liquid phase of 0.8. The point indicated by reference numeral 115 is for a system pressure of 1 mmHg and a relative volatility of 2.1728 shown by the relationship:

$$\alpha = \left[ \frac{Y_v X_{DBE}}{Y_{DBE} X_v} \right].$$

The graph is shown by reference numeral 110. The point indicated by reference numeral 114 is for a system pressure of 10 mmHg and a relative volatility of 2.2696. The point indicated by reference numeral 113 is for a system pressure of 50 mmHg and a relative volatility of 2.3694. The point indicated by reference numeral 112 is for a system pressure of 100 mmHg and a relative volatility of 2.6667. The point indicated by reference numeral 111 is for a system pressure of 200 mmHg and a relative volatility of 3.2727.

The graph 110 shows the relative volatility at a mole fraction of dibenzyl ether in the liquid phase of 0.8 versus $\log_{10}$ of system pressure (indicated by the symbol: $+\log_{10}\Pi$) as follows:

$$\alpha_{54} = 0.79/n_e \left[ \frac{28.8}{\log_{10} \pi + 0.094} \right].$$

FIG. 12 is a schematic diagram of a batch distillation column for the azeotropic distillation of the system vanillin-second chemical-dibenzyl ether. Reference numeral 120 is for the distillation pot. Reference numeral 121 is for the liquid contained in the distillation pot. Reference numeral 122 is for the distillate holding tank. Reference numeral 123 is for the reflux "plate".

The following detailed operating example illustrates the practice of the invention in a preferred form thereby enabling a person of ordinary skill in the art to practice the invention. The principles of this invention, its operating parameters and other obvious modifications thereof will be understood in view of the following detailed procedure. This invention is only limited by the scope of the claims and is not to be limited by the following operating example:

EXAMPLE I

Crude vanillin having the structure:

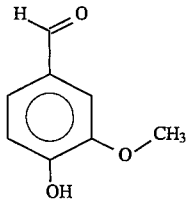

(24.45 parts—64%; 8.7% parahydroxybenzaldehyde and 27.7% non-volatiles being the remainder) and dibenzyl ether having the structure:

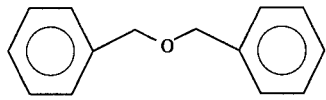

(75.52 parts) are added to a 12 liter, three-neck flask fitted with an overhead mechanical stirrer, electrical heating mantle and thermocouple. After heating the mixture to 100° C. to dissolve the crude vanillin, diatomaceous earth (CELITE® 501) (0.02 parts) is added with stirring. The mixture is then gravity filtered through filter paper (WHATMAN® 113).

Analysis of the resulting filtrate reveals that the vanillin content is 18%. The resulting crude vanillin solution is transferred to a 12 liter flask fitted with a 2 foot vacuum-jacketed glass column (inside diameter: 1.5 inches) packed with structural stainless steel (as illustrated in FIG. 12 described in detail, supra, having seven "plates"). The top of the packed column is fitted with a vertical condenser and reflux head (the "first plate"). The distillate line is also jacketed. The distillate stream is maintained at 60° C. to prevent vanillin from crystallizing out of the stream. The system is arranged to operate under vacuum with dry ice traps. After reducing the pressure to 6–8 mmHg, heating is commenced. Distillation with total takeoff begins when the pot temperature reaches 160° C. and 450 grams of still distillation fractions are collected. Every other fraction is analyzed via gas chromatography techniques. When the vanillin content drops below 10%, the reflux head is activated so that the return distillate (reflux) ratio is 1:1. After this, every time the vanillin content of the distillation drops below 10%, the reflux ratio is increased: first to 2:1, then 5:1 and finally 10:1. Throughout the distillation, the vapor temperature is in the range of 120°–122° C. at 6–8 mmHg. The distillation is terminated when the vanillin content of the distillate drops below 10% using a reflux ratio of 10:1. The pot temperature is about 169° C. at this point.

All fractions with a vanillin content of 5% or greater are bulked into a 5 liter, three-necked flask fitted with an electrical heating mantle, overhead mechanical stirrer and thermocouple. The bulked fractions are heated to 60° C. at which any vanillin that may have crystallized out redissolves. The heating mantle is removed and the flask is allowed to cool under ambient conditions with continued stirring. Vanillin begins to crystallize when the pot temperature drops below 40° C. At this point, the flask is placed in an ice water bath. When the pot temperature reaches 3° C. the mixture is vacuum filtered. The filtrate which contains approximately 5% vanillin is retained for dissolving the next batch of crude vanillin. The filtered vanillin is re-suspended in hexane, filtered and washed with additional hexane. After air drying, slightly off-white vanillin (1,162 grams; purity: 97.5%) is obtained.

Regarding the batch distillation as set forth in Example I, supra, the apparatus for which is set forth in FIG. 12 described in detail, supra, an equation which describes the change in mole fraction of a component in the distillate, for example, vanillin versus the change in the number of moles of vanillin in the distillation pot is as follows:

$$\ln_e \frac{L_1}{L_2} = \frac{1}{\alpha - 1} \ln \left\{ \frac{x_1}{x_2} \frac{(1-x_2)}{(1-x_1)} \right\} + \ln \frac{(1-x_2)}{(1-x_1)}$$

where in $L_1$ is the initial number of moles of vanillin in the pot and $L_2$ is the final number of moles of vanillin in the pot; $\alpha$ represents the relative volatility of the vanillin with respect to the dibenzyl ether shown by the relationship:

$$\alpha = \left[ \frac{Y_v X_{DBE}}{Y_{DBE} X_v} \right];$$

$x_1$ represents the mole fraction of vanillin in the distillate initially; and $x_2$ represents the mole fraction in the vanillin at the end of the distillation. The equation is known as the Raleigh equation and is described in detail in Walker, et al, "Principles of Chemical Engineering", 3rd Edition, McGraw Hill Book Company, 1937 ("Chemical Engineering Series") at pages 532 and 533.

An equation for determination of the number of theoretical plates necessary to effect separation of the azeotrope, the mixture of vanillin and dibenzyl ether from the second chemical, for example, parahydroxybenzaldehyde, is as follows:

$$n = \frac{\log \dfrac{x_o'\left(1 - \dfrac{mc(a-1)}{a - mc^2} x_n'\right)}{x_n'\left(1 - \dfrac{mc(a-1)}{a - mc^2} x_0'\right)}}{\log \dfrac{a}{mc^2}}$$

wherein $x'_0$ represents the initial mole fraction of vanillin in the still pot and $x'_n$ represents the mole fraction of vanillin in the $n^{th}$ plate. $\alpha$ as determined by the relationship:

$$\alpha = \left[ \frac{Y_v X_{DBE}}{Y_{DBE} X_v} \right],$$

is the relative volatility of vanillin with respect to the second chemical and the dibenzyl ether in the still pot. m Is the slope of the slope of the operating line and c is a constant which is a function of the relative volatility. This equation, the "Underwood" equation is set forth in the paper by E. H. Smoker, "ANALYTIC DETERMINATION OF PLATES IN FRACTIONATING COLUMNS", transactions of the *AMERICAN INSTITUTE OF CHEMICAL ENGINEERS*, Volume 34 (No. 5), 1938, pages 165–172, at line 2 on page 169.

Relative Volatility from Wilson Equation:
1 mmHg 0.8 mole fraction Benzyl ether in liquid
A) Physical Properties & given information:

Molar Volume Benzyl ether
$v_{[1]}: = 190.6384615$
Molar Volume Vanillin
$v_{[2]}: = 126.7916667$
Molar Volume Benzyl ether in liquid
$v_{[1]}: = .8$
Molar Volume Vanillin in liquid
$v_{[2]}: = .2$
B) Calculated Vaules:

Temperature is by trial and error; tested by the total pressure calculation:
Temperature C
$t: = 108.87$
Temperature K
$T: = 382.02$
Wilson Coefficient Benzyl ether $$G_{[12]}: = \frac{v_{[2]} e^{-212.0833 \frac{1}{T}}}{v_{[1]}}$$

Wilson Coefficient Vanillin

-continued $$G_{[21]}: = \frac{v_{[1]} e^{-673.5597 \frac{1}{T}}}{v_{[2]}}$$

Activity coefficient for Benzyl ether:

$$\gamma_{[1]}: = e^{-\ln(x_{[1]} + x_{[2]} G_{[12]}) + x_{[2]}\left(\frac{G_{[12]}}{x_{[1]} + x_{[2]} G_{[12]}} - \frac{G_{[21]}}{x_{[2]} + x_{[1]} G_{[12]}}\right)}$$

Activity coefficient for Vanillin:

$$\gamma_{[2]}: = e^{-\ln(x_{[2]} + x_{[1]} G_{[21]}) + x_{[1]}\left(\frac{G_{[12]}}{x_{[1]} + x_{[2]} G_{[12]}} - \frac{G_{[21]}}{x_{[2]} + x_{[1]} G_{[12]}}\right)}$$

Vapor pressure Benzyl ether at 108.87 C. (regressed from simsci data)

$$Psat_{[1]}: = 10^{(8.18117 - 2608.237 \frac{1}{t + 204.92})}$$

Vapor pressure Vanillin at 108.87 C. (regressed from simsci data)

$$Psat_{[2]}: = 10^{(7.97554 - 2363.0437 \frac{1}{t + 179.286})}$$

Total Pressure mmHg (calculated)
$p: = x_{[1]} \gamma_{[1]} Psat_{[1]} + x_{[2]} + x_{[2]} \gamma_{[2]} Psat_{[2]}$
Relative Volatility $$\alpha: = \frac{\gamma_{[1]} Psat_{[1]}}{\gamma_{[2]} Psat_{[2]}}$$

Mole fraction Benzyl ether in vapor $$y_{[1]}: = \frac{\gamma_{[1]} Psat_{[1]} x_{[1]}}{p}$$

Mole fraction Vanillin in vapor $$y_{[2]}: = \frac{\gamma_{[2]} Psat_{[2]} x_{[2]}}{p}$$

wherein G is the same as $\alpha$ set forth, supra, the Wilson coefficients.

What is claimed is:

1. A method for recovering vanillin having the structure:

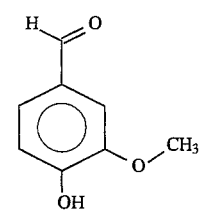

from a mixture of (i) vanillin and (ii) a second organic chemical forming a single liquid phase with said vanillin at a temperature of from 20° C. up to 50° C. at 1 atmosphere pressure which comprises:

(1) distilling a mixture of vanillin and said second organic chemical in the presence of an azeotrope forming agent which is dibenzyl ether having the structure:

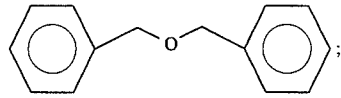

(2) recovering a single phase mixture of vanillin and dibenzyl ether azeotroping agent as overhead distillation product and said second organic chemical from a still pot;

(3) separating said vanillin from said dibenzyl ether azeotrope forming agent by cooling said single phase mixture of vanillin and dibenzyl ether whereby vanillin crystals precipitate from said mixture of vanillin and dibenzyl ether; and (4) separating said vanillin crystals from said single phase mixture of vanillin and dibenzyl ether.

2. The method of claim 8 wherein the second organic chemical is parahydroxybenzaldehyde having the structure:

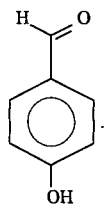

3. The method of claim 1 wherein the step of recovering the single phase of vanillin and dibenzyl ether as overhead distillation product takes place at a temperature of from about 108° C. up to about 152° C. at a system pressure of from about 1 mmHg up to about 10 mmHg.

4. The method of claim 1 wherein the step of recovering the single phase of vanillin and dibenzyl ether as overhead distillation product takes place wherein the mole fraction of dibenzyl ether in a liquid phase and vapor phase varies from about 0.42 up to about 0.53 at a system pressure of from about 1 mmHg up to about 200 mmHg.

* * * * *